(12) United States Patent
Holakovsky et al.

(10) Patent No.: US 10,080,853 B2
(45) Date of Patent: Sep. 25, 2018

(54) NEBULIZER

(75) Inventors: Holger Holakovsky, Witten (DE);
Marc Rohrschneider, Hagen (DE);
Florian Witte, Schwabenheim (DE);
Kevin Peter Deane, Cambridge (GB);
Douglas Ivan Jennings, Cambridge (GB); Charles Henderson, Cambridge (GB)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 274 days.

(21) Appl. No.: 13/476,217

(22) Filed: May 21, 2012

(65) Prior Publication Data

US 2013/0125880 A1 May 23, 2013

(30) Foreign Application Priority Data

May 23, 2011 (EP) .................................. 11004237

(51) Int. Cl.
| | | |
|---|---|---|
| *A61M 15/00* | (2006.01) | |
| *B05B 11/00* | (2006.01) | |
| *A61M 11/02* | (2006.01) | |
| *A61M 11/00* | (2006.01) | |

(52) U.S. Cl.
CPC ...... *A61M 15/0065* (2013.01); *A61M 11/007* (2014.02); *A61M 11/02* (2013.01); *A61M 15/008* (2014.02); *A61M 15/0026* (2014.02); *A61M 15/0081* (2014.02); *B05B 11/0054* (2013.01); *B05B 11/308* (2013.01); *A61M 2202/0468* (2013.01); *A61M 2202/064* (2013.01); *A61M 2205/273* (2013.01); *A61M 2205/52* (2013.01); *A61M 2205/8206* (2013.01)

(58) Field of Classification Search
CPC .......... A61M 15/0065; A61M 15/0081; A61M 11/007; A61M 15/0026; A61M 15/008; A61M 11/02; A61M 2202/0468; A61M 2202/064; A61M 2205/8206; A61M 2205/52; A61M 2205/273; A61M 15/009; A61M 2205/60; A61M 2205/6027; B05B 11/308; B05B 11/0054
USPC ............. 128/200.21, 200.14, 203.12, 200.23
See application file for complete search history.

(56) References Cited

U.S. PATENT DOCUMENTS

| | | | |
|---|---|---|---|
| 4,934,358 A | 6/1990 | Nilsson et al. | |
| 5,284,133 A | 2/1994 | Burns et al. | |
| 5,394,866 A * | 3/1995 | Ritson et al. | ............ 128/200.14 |
| 5,704,792 A * | 1/1998 | Sobhani | ................ H01R 39/64 439/21 |

(Continued)

FOREIGN PATENT DOCUMENTS

| | | |
|---|---|---|
| WO | 92/17231 A1 | 10/1992 |
| WO | 00/01612 A2 | 1/2000 |

(Continued)

*Primary Examiner* — Gregory Anderson
*Assistant Examiner* — Elliot S Ruddie
(74) *Attorney, Agent, or Firm* — David S. Safran

(57) ABSTRACT

A nebulizer is proposed as depicted in exemplary FIG. 7 which comprises a replaceable container, a counting device and a lock for locking the nebulizer against further use. The container is provided with an electronic storage which is electrically connected to the counting device. The nebulizer comprises an electric drive for actuating the lock. This allows secure operation and/or simple handling of the nebulizer.

16 Claims, 7 Drawing Sheets

(56) References Cited

U.S. PATENT DOCUMENTS

| | | | | |
|---|---|---|---|---|
| 6,331,117 B1 * | 12/2001 | Brundage | ............... | H01R 39/64 |
| | | | | 361/728 |
| 7,331,340 B2 * | 2/2008 | Barney | ............. | A61M 15/0065 |
| | | | | 128/200.19 |
| 2002/0000225 A1 * | 1/2002 | Schuler et al. | ........... | 128/200.14 |

FOREIGN PATENT DOCUMENTS

| WO | 02/05879 A1 | 1/2002 |
|---|---|---|
| WO | 02/17988 A2 | 3/2002 |
| WO | 2004/078236 A2 | 9/2004 |
| WO | 2005/080001 A1 | 9/2005 |
| WO | 2007/022898 A2 | 3/2007 |

* cited by examiner

Prior Art

Prior Art

NEBULIZER

The present invention relates to a nebulizer for an inhaler, for a fluid (2), comprising: a replaceable container (3) containing the fluid (2), and a counting device (23) for counting the number of operations with the current container (3) and/or the number of containers (3) that have been used or still can be used WO 2007/022898 A2 discloses a nebulizer which comprises, as a reservoir for fluid which is to be atomized or nebulized, an insertable rigid container having an inner bag containing the fluid and a pressure generator with a drive spring for delivering and atomizing the fluid.

The container can be inserted into a housing of the nebulizer. The housing is closed by a lower housing part. A counting device can be arranged in the housing part. The counting device locks the nebulizer against further use if a predetermined number of operations has been reached or exceeded. Then, the housing part may be replaced together with the counting device and the container. Further, the nebulizer comprises a device for permanently locking the nebulizer when a certain number of containers have been used or when a certain number of operations have been reached.

By rotating the lower housing part the drive spring can be tensioned and fluid can be sucked into a compression chamber of the pressure generator. Simultaneously, the container is moved into the lower housing part in a stroke movement within the nebulizer. After manual operation of a blocking element the drive spring is released and moves a delivery tube into the pressure chamber so that the fluid is put under pressure by the drive spring and is delivered or atomized through a nozzle into a mouthpiece as an aerosol, without the use of propellant gas.

Object of the present invention is to provide a nebulizer allowing easy and/or improved handling and/or secure operation, in particular with multiple and/or different containers.

The above object is achieved by a nebulizer (1), in particular an inhaler, for a fluid (2), comprising:

a replaceable container (3) containing the fluid (2), and a counting device (23) for counting the number of operations with the current container (3) and/or the number of containers (3) that have been used or still can be used, characterized in that the container (3) is provided with an electronic storage (28) and that the nebulizer (1), the container (3) and/or the counting device (23) comprise connecting means (30) for electrically connecting the electronic storage (28), and/or that the nebulizer (1) comprises an electric drive (34) actuating a lock (24), the lock (24) locking the nebulizer (1) against further use in a first locked state when the container (3) has to be replaced and/or when a predetermined number of operations has been reached or exceeded with the current container (3) and/or locking against opening of the nebulizer (1) or container (3) replacement before the first locked state has been reached or in a second locked state.

Preferred embodiments are described below.

According to one aspect of the present invention, the nebulizer comprises a replaceable container which is provided with an electronic storage, wherein the nebulizer or its counting device comprises connecting means for electrically connecting the electronic storage. This allows easy and/or improved handling and/or secure operation, in particular with multiple and/or different containers. In particular, the electronic storage may contain information regarding the fluid contained in the container, such as identification of the fluid or of components of the fluid, volume, date of filling or packaging, date of last use or the like. Alternatively or additionally, the nebulizer or its counting device may store information in the electronic storage, in particular regarding use of the container or its fluid, date and/or time of first use, date and/or time of the last use and/or of all uses, identification of the nebulizer, and/or other parameters of use. Thus, it is easier to monitor or check use or operation of the nebulizer, container and/or fluid.

Preferably, the container is moveable within the nebulizer and/or relative to a housing part of the nebulizer during conveying of the fluid, pressure generation and/or nebulization. This movement is preferably linear and/or stroke-like. Preferably, the connecting means provide the electrical connection to the electronic storage at least only in an end position of the container. This facilitates a simple construction.

According to another aspect of the present invention, the nebulizer comprises an electric drive for actuating a lock, in particular for locking the nebulizer against further use in a first locked state when the container has to be replaced and/or when a predetermined number of operations has been reached or exceeded with the current container and/or for locking against opening of the nebulizer or container replacement before the first locked state has been reached or in a second locked state (final locked state). This allows easy and/or secure operation and, in particular, a simple mechanical construction of the nebulizer.

According to a further aspect of the present invention, all or essentially all components of the nebulizer required for counting and/or locking are arranged in a (lower) housing part of the nebulizer that can be opened and/or separated from the nebulizer for replacing or inserting the container. This allows in particular a simple construction and/or adaptation of the nebulizer to different requirements as it is relatively simple to adapt or change only the housing part.

The above aspects of the present invention and the further aspect described below can be realized independently from each other, and in any combination.

BRIEF DESCRIPTION OF THE DRAWINGS

Further advantages, features, characteristics and aspects of the present invention will become apparent from the claims and the following description of a preferred embodiment with reference to the drawings. It shows:

In the Figures, the same reference numerals are used for identical or similar parts, resulting preferably in corresponding or comparable properties and advantages, even if the associated description is not repeated.

DETAILED DESCRIPTION

Figure 1:
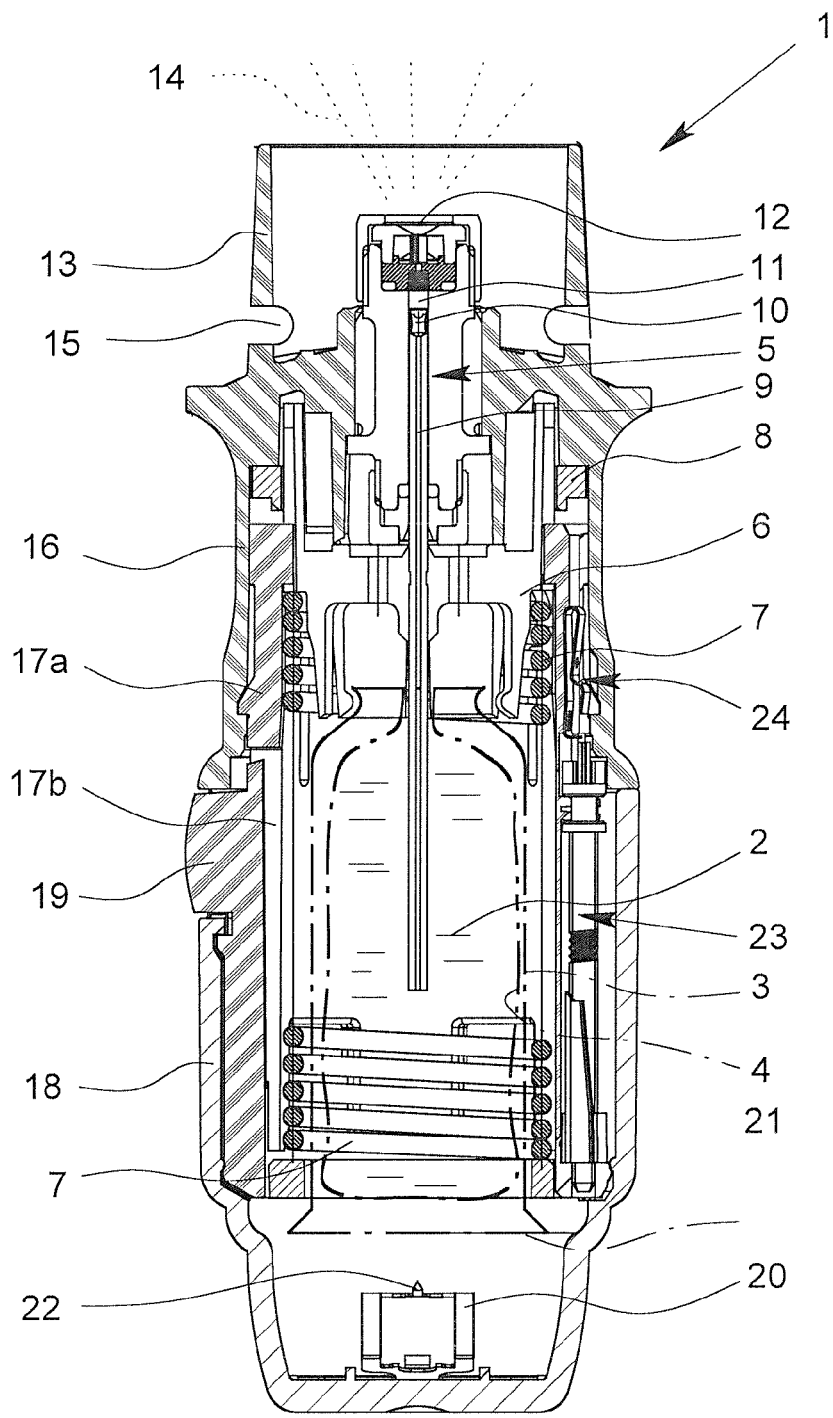
FIG. 1 a schematic section of a known nebulizer in a non-tensioned state.
Figure 2:
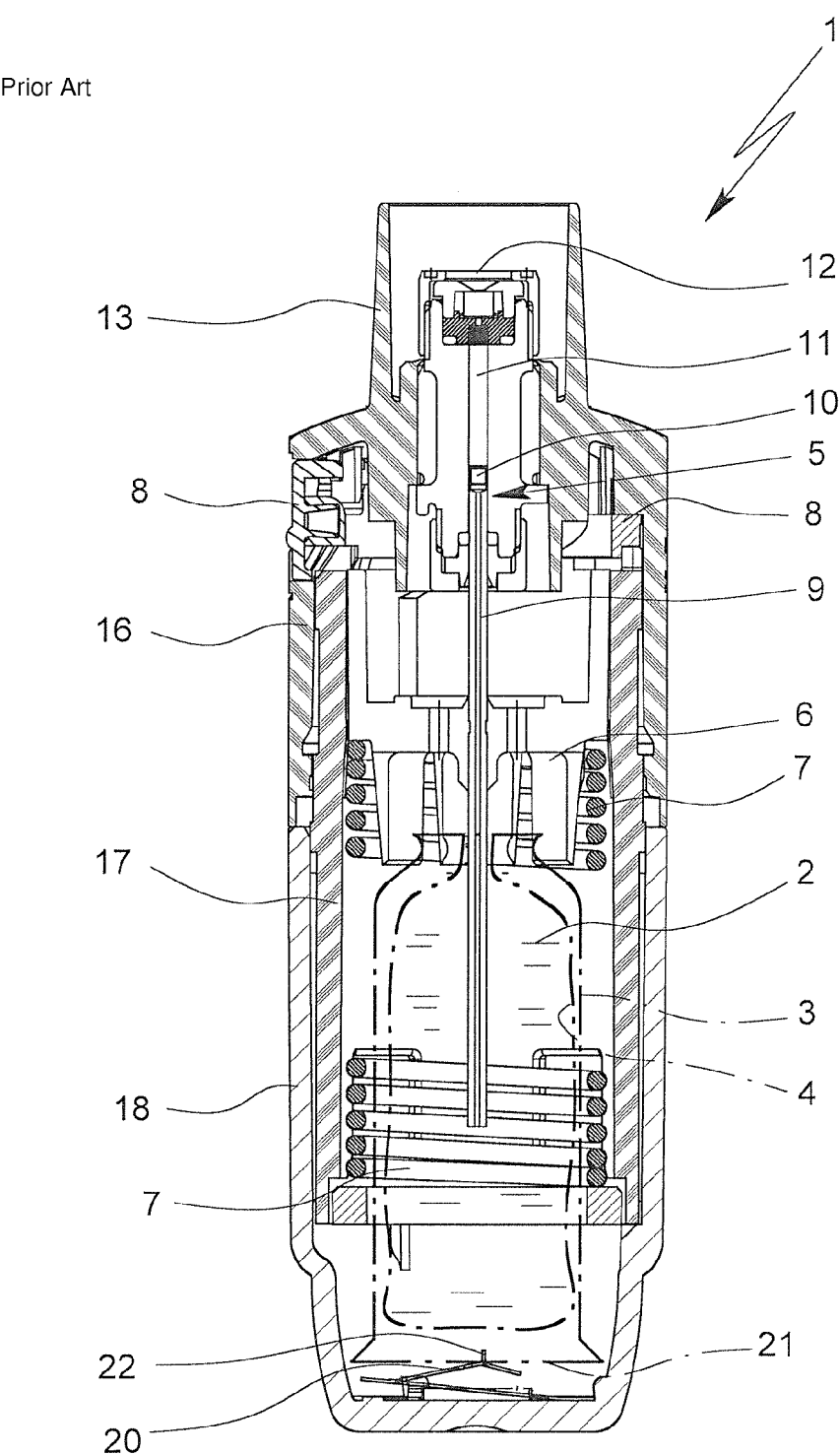
FIG. 2 a schematic section, rotated 90° compared with FIG. 1, of the known nebulizer in a tensioned state.

FIGS. 1 and 2 show a known nebulizer 1 for atomizing a fluid 2, particularly a highly effective pharmaceutical composition, medicament or the like, diagrammatically shown in a non-tensioned state (FIG. 1) and in a tensioned state (FIG. 2). The nebulizer 1 is constructed in particular as a portable inhaler and preferably operates only mechanical and/or without propellant gas.

When the fluid 2, preferably a liquid, more particularly a pharmaceutical composition, is nebulized, an aerosol 14 (FIG. 1) is formed, which can be breathed in or inhaled by a user. Usually the inhaling is done at least once a day, more particularly several times a day, preferably at set intervals, depending on the complain or illness from which a patient is suffering.

The nebulizer 1 is provided with or comprises an insertable or replaceable container 3 containing the fluid 2. The container 3 thus forms a reservoir for the fluid 2, which is to be nebulized. Preferably, the container 3 contains multiple doses of fluid 2 or active substance in particular sufficient to provide up to 200 dosage units or doses, for example, i.e. to allow up to 200 sprays or applications. A typical container 3, as disclosed in WO 96/06011 A1, holds e.g. a volume of about 2 to 20 ml.

It has to be noted that the dose can vary, in particular depending on the fluid 2 or medicament. The nebulizer 1 can be adapted respectively.

Further, the number of doses contained in the container 3 and/or the total volume of the fluid 2 contained in the container 3 can vary depending on the fluid 2 or respective medicament and/or depending on the container 3 and/or depending on the necessary medication or the like.

Preferably, the container 3 can be replaced or exchanged, wherein the number of containers 3, which can be used with the same nebulizer 1, is preferably restricted, e.g. to a total number of four or five containers 3.

The container 3 is preferably substantially cylindrical or cartridge-shaped and once the nebulizer 1 has been opened the container 3 can be inserted therein preferably from below and changed if desired. It is preferably of rigid construction, the fluid 2 in particular being held in a collapsible bag 4 in the container 3.

The nebulizer 1 comprises preferably a pressure generator 5 for conveying and nebulizing the fluid 2, particularly in a preset and optionally in an adjustable dosage amount. The pressure generator 5 comprises preferably a holder 6 for releasable holding the container 3, a drive spring 7 associated to the holder 6, only partly shown, a blocking element 8 which can catch and block the holder 6 and can be manually operated to release the holder 6 allowing drive spring 7 to expand, a conveying element, such as a conveying tube 9, a non-return valve 10, a pressure chamber 11 and/or a nozzle 12 for nebulizing the fluid 2 into a mouthpiece 13. The completely inserted container 3 is fixed or held in the nebulizer 1 via the holder 6, in particular when or with completely closing the nebulizer 1 or housing part 18, such that the conveying tube 9 penetrates into the container 3. The holder 6 is preferably constructed so that the container 3 can be exchanged.

When the drive spring 7 is axially tensioned in the tensioning process the holder 6 with the container 3 and the conveying tube 9 are moved downwards in the drawings and fluid 2 is sucked out of the container 3 into the pressure chamber 11 of the pressure generator 5 through the non-return valve 10. In this state, the holder 6 is caught by the blocking element 8 so that the drive spring 7 is kept compressed. Then, the nebulizer 1 is in the so-called activated or tensioned state.

During the subsequent relaxation in the nebulization process after actuation or pressing of the blocking element 8 the fluid 2 in the pressure chamber 11 is put under pressure as the conveying tube 9 with its now closed non-return valve 10 is moved back in the pressure chamber 11, here in the drawings upwards, by the relaxation or force of the drive spring 7 and now acts as a pressing ram or piston. This pressure forces the fluid 2 through the nozzle 12, whereupon it is nebulized into the aerosol 14, as shown in FIG. 1.

Generally, the nebulizer 1 operates with a spring pressure of 5 to 200 MPa, preferably 10 to 100 MPa on the fluid 2, and/or with a volume of fluid 2 delivered per stroke of 10 to 50 µl, preferably 10 to 20 µl, most preferably about 15 µl. The fluid 2 is converted into or nebulized as aerosol 14, the droplets of which have an aerodynamic diameter of up to 20 µm, preferably 3 to 10 µm. Preferably, the generated jet spray has an angle of 20° to 160°, preferably 80° to 100°. These values also apply to the nebulizer 1 according to the teaching of the present invention as particularly preferred values.

A user or patient (not shown) can inhale the aerosol 14, preferably while an air supply can be sucked into the mouthpiece 13 through at least one optional air supply opening 15.

Preferably, the nebulizer 1 or drive spring 7 can be manually activated or tensioned, in particular by actuation of an actuation member.

The nebulizer 1 comprises preferably an upper housing part 16 and an inner part 17 which is rotatable relative thereto (FIG. 2) having an upper part 17a and a lower part 17b (FIG. 1), while an in particular manually operable (lower) housing part 18 is releasable fixed, particularly fitted or held onto the inner part 17, preferably by means of a retaining element 19. Preferably, the housing parts 16 and 18 form a housing of the nebulizer 1. In order to insert and/or replace the container 3 the housing can be opened and/or the housing part 18 can be detached from the nebulizer 1 or its housing.

The actuation member, preferably the housing part 18, can be actuated, here rotated relative to the upper housing part 16, carrying with it or driving the inner part 17. As a result the drive spring 7 is tensioned in the axial direction by means of a gear or transmission (not shown) formed between the inner part 17, in particular its upper part 17a, and the holder 6 and acting on the holder 6. During tensioning the container 3 is moved axially downwards until the container 3 assumes an end position as shown in FIG. 2. In this activated or tensioned state the drive spring 7 is under tension and can be caught or held by the blocking member 8. During the nebulizing process the container 3 is moved back into its original position (non-tensioned position or state shown in FIG. 1) by the drive spring 7. Thus the container 3 executes a lifting or stroke or linear movement or a back and forth movement during the tensioning process or conveying of fluid 2 and/or during the pressure generation nebulization (process).

The housing part 18 preferably forms a cap-like lower housing part and fits around or over a lower free end portion of the container 3. As the drive spring 7 is tensioned the container 3 moves with its end portion (further) into the housing part 18 or towards the end face thereof, while an aeration means, such as an axially acting spring 20 arranged in the housing part 18, comes in contact with base 21 of the container 3 and pierces the container 3 or a base seal thereon with a piercing element 22 when the container 3 makes contact with it for the first time, to allow air in or aeration.

The nebulizer 1 comprises preferably a counting device 23, which counts the actuations or operations (uses) of the nebulizer 1, preferably by detecting its tensioning or the rotation of the inner part 17 relative to the upper part 16 of the housing. Preferably, the counting device 23 or a lock 24 (preferably formed by a locking spring as shown in FIG. 1 and actuated by the counting device 23) locks the (further) actuation or use of the nebulizer 1, e.g. blocks further rotation of the housing part 18/inner part 17 and, thus, tensioning of the nebulizer 1 or its drive spring 7 and/or blocks actuation of the blocking element 8, when a certain number of actuations or operations or discharged doses has been reached or exceeded.

In the following, a preferred embodiment of the nebulizer 1 according to the present invention will be described in more detail with reference to the further Figures, wherein only essential differences from the nebulizer 1 described above will be emphasized or described. Thus, the remarks relating to FIGS. 1 and 2 apply preferably accordingly or in a similar manner, while any desired combinations of features are possible.

Figure 3:
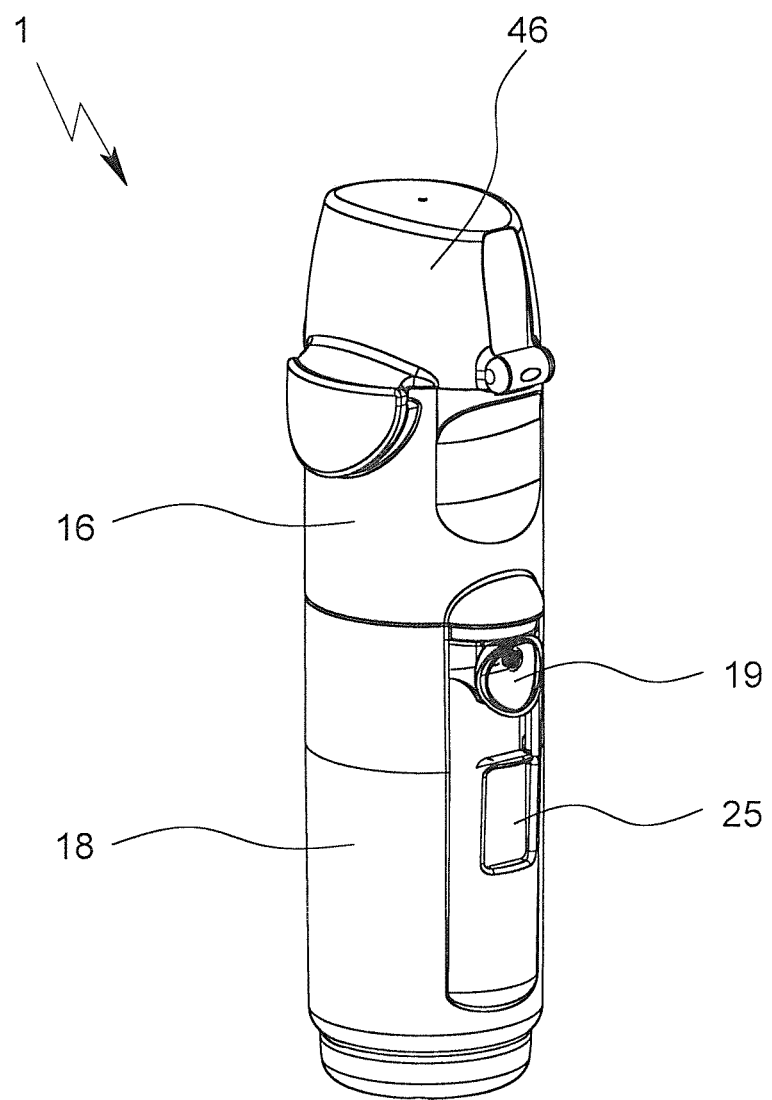
FIG. 3 a schematic perspective view of a nebulizer according to the present invention.

FIG. 3 shows the nebulizer 1 in a perspective side view with mounted (lower) housing part 18. The nebulizer 1, the housing part 18 or counting device 23 comprises a display 25 which is visible from the outside. The display 25 is preferably held by or integrated into the housing part 18. However, other constructional solutions are possible as well.

Figure 4:
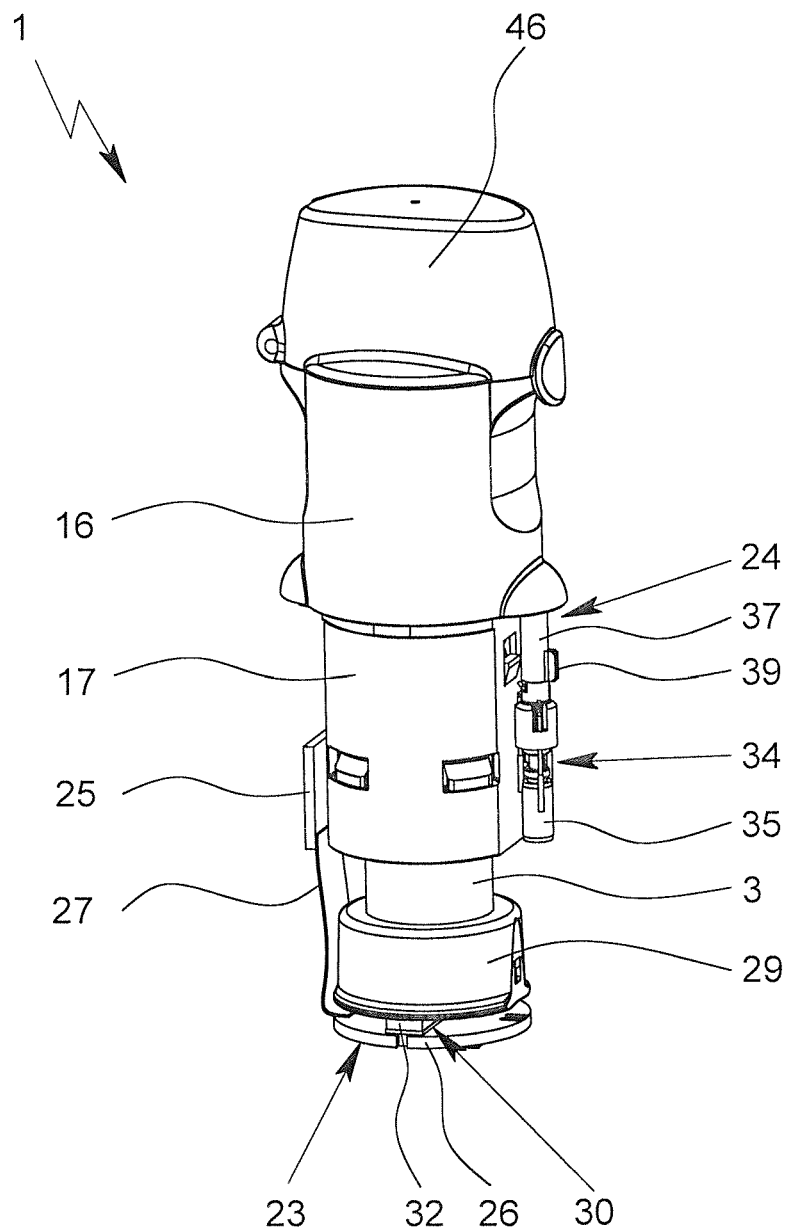
FIG. 4 a schematic view of the nebulizer according to FIG. 3 with a cut-away housing part and with a container.

Preferably, the counting device 23 and/or lock 24 are arranged—at least essentially—at or within the housing part 18. FIG. 4 shows the nebulizer 1 in another perspective side view with cut-away housing part 18 so that the counting device 23, the lock 24 and the display 25 are visible.

Preferably, the counting device 23 and/or display 25 work electronically. In particular, the display 25 is connected with the counting device 23, more particularly with a circuit board 26 of the counting device 23, via a cable 27 as indicated in FIG. 4. Preferably, the counting device 23 or circuit board 26 controls the display 25, in particular for showing or displaying information, such as a number of operations that have been performed or still can be performed with the current container 3, a number of containers 3 that have been or still can be used with or inserted into the nebulizer 1, information relating to the nebulizer 1 or fluid 2, e.g. about a blocking or locking state of the nebulizer 1, and/or instructions for handling the nebulizer 1, e.g. for replacing the container 3, or the like. The shown information can change if desired. Alternatively or additionally, the display 25 can be used to control the counting device 23. In this case, the display 25 is preferably formed by a touch screen.

Figure 5:
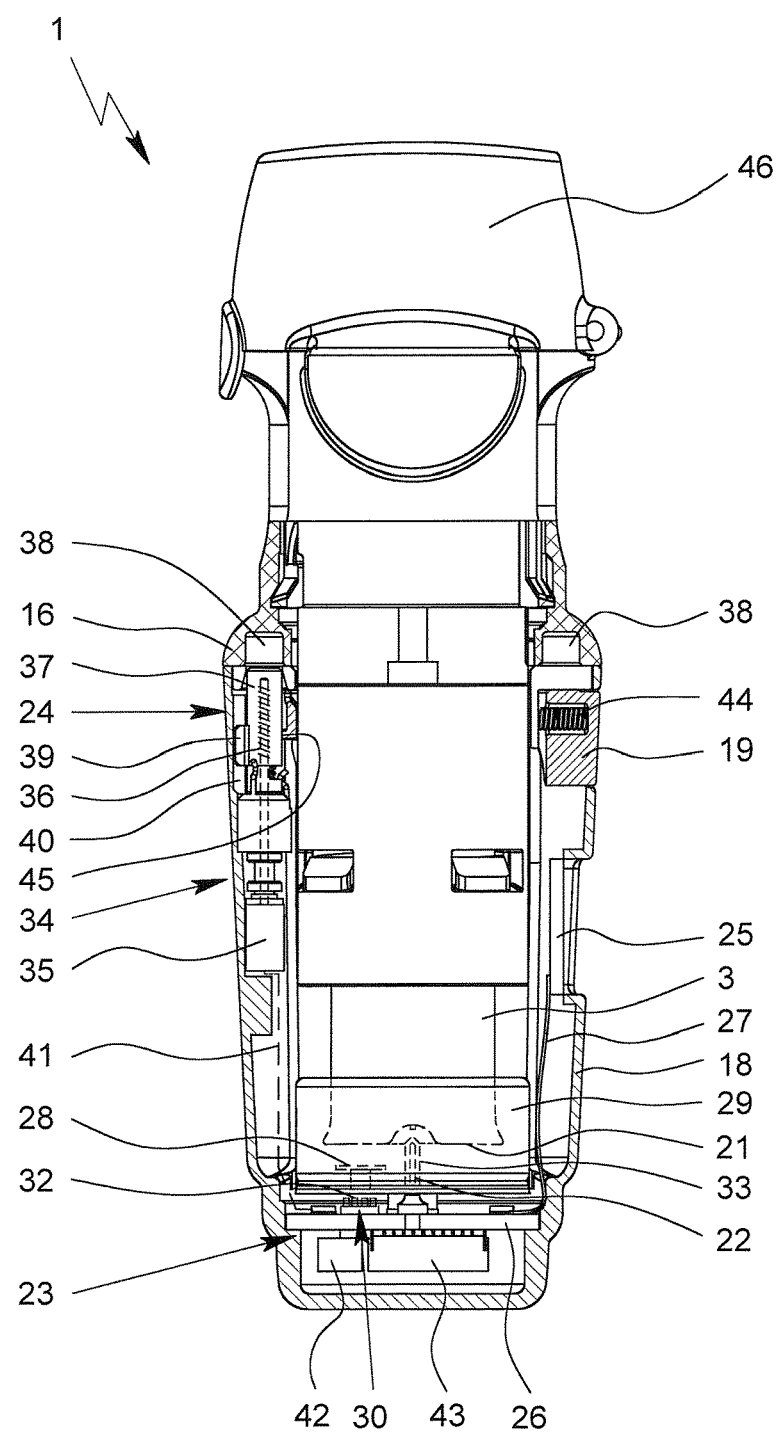
FIG. 5 a schematic section of the nebulizer according to FIG. 3.

Preferably, the counting device 23 or circuit board 26 is located at or adjacent to a bottom or axial end of the housing part 18 and/or clipped into the housing part 18, as schematically shown in the schematic section of the nebulizer 1 according to FIG. 5.

Preferably, the nebulizer 1 or container 3 is provided with an electronic storage 28 as indicated in the schematic section of FIG. 5. Preferably, the electronic storage is electrically erasable, programmable and/or for read-only. In particular, the electronic storage 28 is formed by or comprises a so-called EEPROM. In particular, the electronic storage 28 is associated to and preferably rigidly connected to the container 3 and/or is inseparable from the container 3.

In the present embodiment, the electronic storage 28 is mounted at or to the container 3 by means of a holding element 29. Preferably, the holding element 29 is ring-like and/or encompasses one end and/or the base 21 of the container 3. Preferably, the holding element 29 is connected with the container 3 via a form-fit and/or encompasses a lower edge of the container 3. Preferably, the holding element 29 is inseparably or rigidly fixed to the container 3 and/or moves together with the container 3.

Preferably, the holding element 29 is made of plastics and/or molded, in particular directly on the container 3. However, the storage 28 and/or holding element 29 can be attached to the container 3 alternatively or additionally in any other suitable manner, e.g. by gluing, clamping or the like.

Holding element 29 may form a grip for holding the container 3 and/or for pulling the container 3, in particular for detaching the container 3 or pulling the container 3 out of the inner part 17.

Preferably, the nebulizer 1, the container 3 and/or the counting device 23 comprise connecting means 30 (shown only schematically in FIG. 5) for electrically connecting the electronic storage 28, in particular with the counting device 23 or its circuit board 26.

In the present embodiment, the electronic storage 28, the holding element 29 and/or the connecting means 30 are located at or adjacent to axial end or base 21 of the container 3.

As the container 3 is moveable, in particular back and forth within the nebulizer 1 and/or relative to the housing part 18 during conveying of the fluid 2, biasing of the drive spring 7, pressure generation and/or nebulization, the connecting means 30 is adapted to allow a respective movement of the electronic storage 28 associated to the container 3 relative to the counting device 23 or its circuit board 26 associated to the housing of the nebulizer 1, in particular the housing part 18. In the present embodiment, the connecting means 30 is adapted to provide the electrical connection to the electronic storage 28 at least or only in an end position, in particular the lower position or the position with tensioned drive spring 7, of the container 3. This allows a simple construction.

Figure 6:
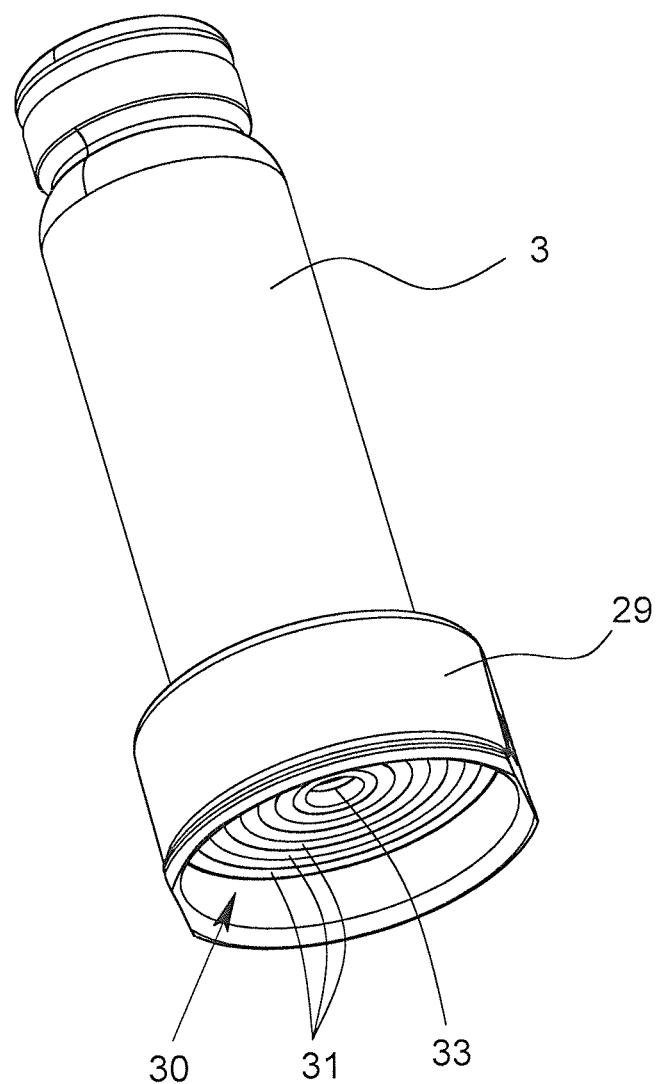
FIG. 6 a perspective view of the container.

In the present embodiment, the connecting means 30 comprises preferably one or more conductors 31 and/or wipers 32. In particular, multiple conductors 31 are arranged ring-like and/or coaxially, preferably on the lower end face of the container 3 or holding element 29 as shown in the perspective view of the separate container 3 according to FIG. 6. In particular, the conductors 31 are arranged in a common plane and/or offset axially against a lower or free edge of the holding element 29.

Preferably, the holding element 29 comprises or is provided with a central or through hole 33 so that the piercing element 22, which is preferably held by the counting device 23 or circuit board 26, can extend through the holding element 29 to pierce or vent the container 3 when moved into its lower position as shown in FIG. 5. Preferably, the conductors 31 are arranged coaxially around this hole 33.

Figure 7:
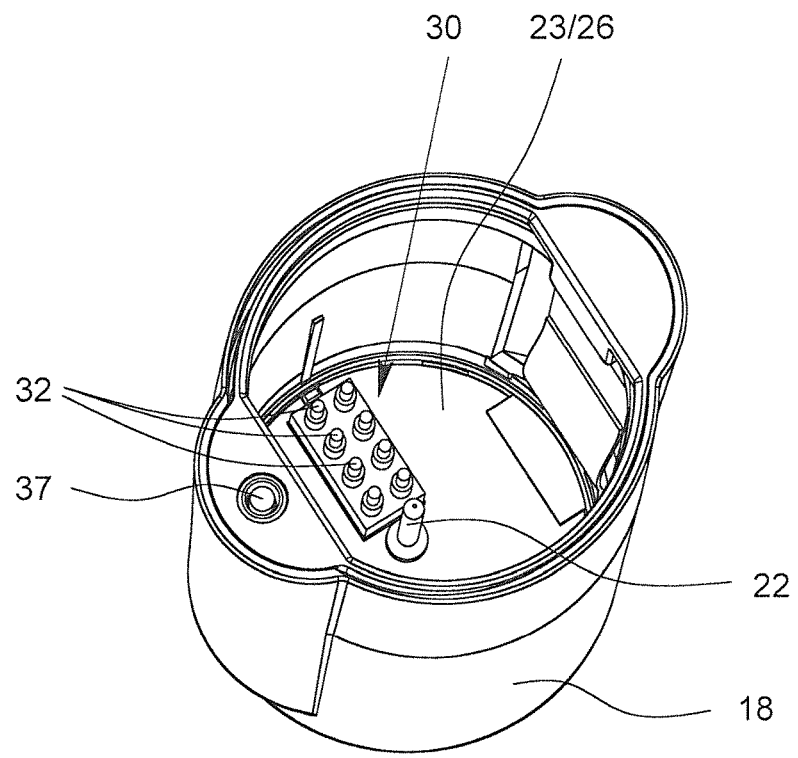
FIG. 7 a perspective view of the housing part.

FIG. 7 shows a perspective view of the separated housing part 18 from above. The piercing element 22, the circuit board 26 and an arrangement of wipers 32 are visible in the housing part 18, in particular on the bottom in the housing part 18. Preferably, pairs of wipers 32 are provided to ensure a secure electrical contact to one associated conductor 31.

Preferably, the wipers 32 are biased upwards and/or against the container 3 or conductors 31. This secures good electrical contact (at least when the container 3 is in its lower position and/or in the tensioned position).

The wipers 32 are preferably supported by and/or electrically connected to or with the connecting device 23 or circuit board 26. The conductors 31 are electrically connected to the electronic storage 28. Thus, the conductors 31 and wipers 32 allow an electric connection of the electronic storage 28 with the counting device 23 or circuit board 26 or vice versa, at least when the container 3 is in its lower position.

Preferably, the counting device 23 or its circuit board 26 is clipped into the housing part 18. However, the circuit board 26 can be connected to or within the housing part 18 in any other suitable manner as well.

Preferably, the nebulizer 1 comprises an electric drive 34 actuating the lock 24. The electric drive 34 is schematically shown in FIG. 4. The electric drive 34 comprises preferably an electric motor 35 and an associated (threaded) spindle 36 as schematically indicated in FIG. 5.

The lock 34 comprises preferably a locking element 37 for engaging into a locking recess 38 in a locked state. FIG. 5 shows the locking element 37 in a non-engaging state.

The locking element 37 is preferably (linearly) moveable between the position engaging into the respective locking recess 38 and the non-engaging position and vice versa, in particular by means of the electric drive 34. In the present embodiment, the locking element 37 meshes with the spindle 36 so that the locking element 37 can be moved (axially) by the respective turning of the spindle 36 by means of the motor 35.

The locking element 37 is preferably provided with a non-circular outer contour or cross section or with a radial protrusion 39 that is guided in an axial groove 40 or the like so that the locking element 37 can move axially or linearly, but is prevented from turning together with the spindle 36. However, other constructional solutions are possible as well.

Preferably, the nebulizer 1 or upper housing part 16 comprises multiple, here two recesses 38 to allow blocking of the nebulizer 1 or lower housing part 18 in different rotational positions, in particular in two positions, preferably offset by 180°, as the housing part 18 can be rotated preferably in 180° steps for tensioning the drive spring 7 and/or conveying the fluid 2 into the pressure chamber 11.

The lock 24 or locking element 37 can lock the nebulizer 1 in a locked state, preferably against using the nebulizer 1, in particular against tensioning the drive spring 7 and/or turning the housing part 18 and/or against actuating or pushing the blocking element 8. In particular, the lock 24 or locking element 37 can block turning of the (lower) housing part 18 and, thus, of the inner part 17 relative to the upper housing part 16. Preferably, the lock 24 or locking element 37 is arranged or located or guided at the housing part 18 and engages into the upper housing part 16 of the nebulizer 1 or in the recess 38 (which is preferably formed in the upper housing part 16) in a locked state or vice versa.

The lock 24 is preferably operated or actuated electrically. With other words, the lock 24 works preferably electrically, here by means of the electric drive 34.

Preferably, the counting device 23 controls the lock 24, in particular the electric drive 34. In particular, the electric drive 34 is connected to the counting device 23 or its circuit board 26 by a cable 41 as schematically indicated in FIG. 5.

The nebulizer 1 or counting device 23 comprises preferably a battery 42 for power supply. This battery 42 may be rechargeable or replaceable, if desired.

The nebulizer 1 or counting device 23 may comprise an integrated circuit, storage and/or microprocessor 43 as schematically indicated in FIG. 5. Preferably, relevant components such as the battery 42 and/or the integrated circuit, storage and/or microprocessor 43, any connectors for the cables 27 and 41 or the like, are connected with and/or held by the circuit board 26.

Preferably, the nebulizer 1 can be blocked against opening or container replacement, in particular against the removing or detaching the lower housing part 18. This is called "opening blocking" in the following.

The opening blocking is preferably controlled by the lock 24, the locking element 37 and/or the electric drive 34. In the present embodiment, the retaining element 19, which has to be depressed—in particular against a force of a spring 44—for detaching the housing part 18 from the nebulizer 1 or inner part 17, can be blocked by the lock 24 or locking element 37 against depressing. For this purpose, the retaining element 19 or an associated portion may extend around the inner part 17 adjacent to the locking element 37 and, for example, may comprise a counter surface or stop 45 that can abut at the locking element 37 or can be blocked by the locking element 37 so that depressing and/or radial displacement of the retaining element 19 can be prevented as shown in FIG. 5 depending on the position of the locking element 37 for realizing the opening blocking. However, other constructional solutions are possible as well, such as axial displacement of retaining element 19.

When the container 3 is inserted and/or the nebulizer 1 is tensioned for the first time after inserting the container 3 or a new container 3, the electronic storage 28 can be read, in particular by the device 23 via the connecting means 30. Thus, information stored in the electronic storage 28 can be considered, processed and/or displayed, in particular via display 25. The information can include information about the fluid 2 contained in the container 3, filling date, any previous use(s) of the container 3 or the like. For example, when the container 3 has already been used, it is possible that its first or last use has been stored in the electronic storage 28 and can prevent further use with the present, the same and/or another nebulizer 1.

Preferably, the display 25 is used to guide a user or patient (not shown). For this purpose, respective instructions can be displayed, in particular when the nebulizer 1 has to be used or primed multiple times before using the first, when the container 3 has to be replaced and/or when the nebulizer 1 has been finally locked or blocked against any further use.

Additionally or alternatively, the display 25 can display the number of uses or operations of the nebulizer 1 that have been performed or still can be performed with the current container 3 or with all containers 3, and/or the number of containers 3 that have been used or inserted or can still be used or inserted.

Preferably, the counting device 23 counts or detects uses or operations of nebulizer 1, in particular by detecting or counting tensioning of the nebulizer 1 or its drive spring 7, rotation of housing part 18 or inner part relative to the upper housing part 16, fluid conveying, fluid atomization, pressure generation, actuation of the locking element 8, any other actuation, movement of the container 3, and/or the like. In particular, the counting device 23 detects or counts movement of the container 3, in particular the stroke of the container 3 when tensioning the drive spring 7 and/or during fluid conveying or sucking from the container 3.

In the present embodiment, the counting device 23 detects or counts preferably each time when the container 3 reaches its lower position or the tensioned position. Preferably, this is detected or counted by means of the connecting 30 or wipers 32 and/or by means of a micro switch, proximity switch or the like. In particular, when the nebulizer 3 reaches the tensioned position, one or more conductors 31 are electrically connected with one or more wipers 32 so that a closed electrical loop and/or an electrical connection to the electronic storage 28 can be established and detected and, accordingly, counted as a use or operation of the nebulizer 1. However, other kinds of detection and counting are possible additionally or alternatively.

If desired, each use or operation of the nebulizer 1 or container 3 can be stored in the electronic storage 28. In addition, it is possible to store additional data such as date, time, first use, last use and/or the like in the electronic storage 28 and/or in the counting device 23. For this purpose, the counting device 23 may comprise a respective time base or the like.

After inserting a container 3 and, if necessary, after priming, the nebulizer 1 can be used with the container 3. In this state, opening blocking is preferably active, in particular by respective movement of the locking element 37 in a position that blocks the retaining element 19 against depressing.

The counting device 23 counts the uses or operations of the nebulizer 1 with the current container 3, in particular as already explained above. When a predetermined number of operations has been used or exceeded, i.e. when a predetermined number of doses of fluid 2 or more has been discharged, the nebulizer 1 enters the first locked state in which the nebulizer 1 is locked against further use with the current container 3. This locking is achieved by the lock 24 by locking the housing part 18 against any further rotation and/or by engaging the locking element 37 into the respective locking recess 38.

In the first locked state, the locking element 37 is moved in a position such that it locks the nebulizer 1 against further use or tensioning, but deactivates the opening blocking. For this purpose, the locking element 37 may be moved axially so far into the recess 37 that the stop 45 can pass or can move into a depression of the locking element 37 or the like so that the retaining element 19 can be depressed to open the nebulizer 1 and replace the container 3.

It is possible to replace the container 3 together with the housing part 18 and the counting device 23. However, preferably the container 3 is replaced and the same housing part 18 and counting device 23 are used again, wherein the new container 3 is preferably inserted into the housing 18 in a first step and, then, the housing part 18 is reconnected to the nebulizer 1. In this case, the counting device 23 detects replacement of the container 3, in particular by establishing an electric contact (which could also be used for counting the containers 3 and uses of the nebulizer 1), e.g. electrically connecting the electronic storage 28 of the new container 3 and/or in any other suitable manner, e.g. by means of a micro switch or the like. Then, the lock 24 is unlocked or deactivated and the opening blocking is activated again, in particular by returning the locking element 37 into its non-engaging position by means of the electric drive 34. Then, the nebulizer 1 can be used with the new container 3 as already described.

The nebulizer 1 is preferably provided with a so-called life span blocking. This means that the nebulizer 1 cannot be used anymore and, in particular, any further container replacement is not further possible. This finally blocked state is called second locked state in the present invention.

The second locked state is entered when a predetermined number of containers 3 have been inserted and used in the nebulizer 1. Preferably, when the number of operations or uses of the last container 3 reaches or exceeds a predetermined number, the lock 24 or locking element 37 locks the nebulizer 1 against further use, but does not deactivate opening blocking. This can be achieved e.g. in that the locking element 37 is moved not so far into recess 37 such that the stop 45 cannot pass and the retaining element 19 cannot be depressed so that opening of the nebulizer 1 and container replacement are not possible.

With other words, the lock 24 and/or first locked state can be reset if the container 3 is or has been replaced. However, the lock 24 and/or first locked state are blocked against resetting in the second locked state.

It has to be noted that FIGS. 3 to 5 show the nebulizer 1 with a cover 46 covering the mouth piece 13. This cover 46 can be removed or opened for using the nebulizer 1.

As already mentioned, individual features, aspects and/or principles of the embodiment described may also be combined with one another if desired and may be used particularly in the nebulizer according to FIGS. 1 and 2 but also in similar or different nebulizers.

Unlike freestanding equipment or the like the proposed nebulizer 1 is preferably designed to be portable and in particular is a mobile hand operated device.

The proposed solution may, however, be used not only in the nebulizers 1 specifically described here but also in other nebulizers or inhalers, e.g. powder inhalers or so-called metered dose inhalers.

Preferably, the fluid 2 is a liquid, as already mentioned, especially an aqueous pharmaceutical formulation or an ethanolic pharmaceutical formulation. However, it may also be some other pharmaceutical formulation, a suspension or the like.

According to an alternative embodiment the fluid 2 may also comprise particles or powder. In this case, instead of the expulsion nozzle 12, some other kind of supply device may be provided, especially an expulsion opening (not shown) or a supply channel (not shown) for supplying the fluid or powder or the like into the mouthpiece 13. The optional air supply opening 15 then serves to supply ambient air preferably in parallel so as to general or allow an airflow with a sufficient volume for breathing in or inhaling through the mouthpiece 13.

If necessary the fluid 2 may also be atomized by means of a propellant gas.

Preferred ingredients and/or formulations of the preferably medicinal fluid 2 are listed in particular in WO 2009/115200 A1, preferably pages 25 to 40, which is incorporated herewith by reference. In particular, these may be aqueous or non-aqueous solutions, mixtures, formulations containing ethanol or free from solvent, or the like.

LIST OF REFERENCE NUMERALS 1 nebulizer
2 fluid
3 container
4 bag
5 pressure generator
6 holder
7 drive spring
8 blocking element
9 conveying tube
10 non-return valve
11 pressure chamber
12 nozzle
13 mouthpiece
14 aerosol
air supply opening
16 upper housing part
17 inner part
17a upper part of the inner part
17b lower part of the inner part
18 housing part (lower part)

19 retaining element
20 spring
21 base
22 piercing element
23 counting device
24 lock
25 display
26 circuit board
27 cable
28 storage
29 holding element
30 connecting means
31 conductor
32 wiper
33 hole
34 electric drive
35 motor
36 spindle
37 locking element
38 locking recess
39 protrusion
40 groove
41 cable
42 battery
43 micro processor
44 spring
45 stop
46 cover

What is claimed is:

1. Nebulizer which is an inhaler for a fluid, comprising:
a nebulizer housing,
an electronically actuatable locking device for locking the nebulizer,
a replaceable container containing the fluid having a base end and a dispensing end at opposite ends of the container from each other, and
a counting device for counting how many operations have been performed with the current container and/or how many containers have been used or still can be used and for controlling the locking device, said counting device being affixed within the nebulizer housing and having electrical contacts which face the base end of the replaceable container when inserted in the nebulizer housing,
wherein the container is provided with an electronic storage thereon and the container comprises connecting means for electrically connecting the electronic storage to the counting device, wherein the connecting means is affixed directly to the base end of the replaceable container facing said electrical contacts of the counting device, the connecting means connecting to the counting device only in a position of the container in which the base end is displaced toward an inner axial end of the nebulizer housing, and
wherein the connecting means comprises a plurality of conductors and/or wipers arranged in a ring-shaped pattern formed of concentric rings located one within another in a common plane,
wherein the counting device is adapted to control locking of the locking device based on data stored in the electronic storage of the replaceable container.

2. Nebulizer according to claim 1, wherein the electronic storage (28) is electrically erasable, programmable and/or an electrically erasable, programmable read-only memory (EEPROM).

3. Nebulizer according to claim 1, wherein the electronic storage (28) is inseparable from the container.

4. Nebulizer according to claim 1, wherein the counting device controls or operates the locking device via an electric drive.

5. Nebulizer according to claim 4, wherein the electric drive comprises an electric motor and an associated spindle so that a locking element meshing with the spindle can be moved axially.

6. Nebulizer according to claim 4, wherein the nebulizer comprises a battery for supplying energy to the electric drive.

7. Nebulizer according to claim 1, wherein the locking device locks the nebulizer in a first locked state against conveying fluid into a pressure generator and/or against tensioning of an energy store which is a drive spring of the nebulizer.

8. Nebulizer according to claim 7, wherein the first locked state is reset by resetting the locking device if the container has been replaced.

9. Nebulizer according to claim 8, wherein the locking device and/or first locked state is blocked against resetting when, in a second locked state, a predetermined number of containers has been used or inserted into the nebulizer.

10. Nebulizer according to claim 1, wherein the nebulizer housing can be detached or opened for replacing the container.

11. Nebulizer according to claim 10, wherein the counting device is arranged inseparable from the housing part.

12. Nebulizer according to claim 4, wherein the locking device and/or the electric drive (34) are arranged inseparable from the housing part (18).

13. Nebulizer according to claim 1, wherein the counting device counts the movement of the container and the connecting means provide the electrical connection to the electronic storage only in an end position of the container.

14. Nebulizer according to claim 1, wherein the nebulizer comprises an electric drive actuating the locking device for locking the nebulizer against further use in a first locked state when the container has to be replaced and/or when a predetermined number of operations has been reached or exceeded with the current container and/or locking against opening of the nebulizer or container replacement before the first locked state has been reached or in a second locked state.

15. Nebulizer which is an inhaler for a fluid, comprising:
a nebulizer housing,
an electronically actuatable locking device for locking and unlocking the nebulizer,
a replaceable container containing the fluid having a bottom end and a dispensing end, and
a counting device for counting how many operations have been performed with the current container and/or how many containers have been used or still can be used,
wherein the nebulizer comprises an electric drive actuating a lock having first and second locked states, the lock locking the nebulizer against further use in a first locked state when the container has to be replaced or when a predetermined number of operations has been reached or exceeded with the current container, the lock being blocked against resetting in the second locked state, thereby locking against opening of the nebulizer or container replacement,
wherein an electronic storage is affixed directly to the replaceable container,
wherein the counting device is located in a bottom area of the nebulizer housing which faces the bottom end of the replaceable container when the replaceable container is inserted in the nebulizer housing, and wherein connecting means is provided which electrically connects the storage of the replaceable container with the counting device, the connecting means being mounted on the bottom end of the replaceable container facing the bottom area of the nebulizer housing and connecting to the counting device only in a position of the container in which the bottom end of the container is displaced toward the bottom area of the nebulizer housing, wherein the connecting means comprises a plurality of conductors and associated wipers arranged in a ring-shaped pattern formed of concentric rings located one within another in a common plane, and wherein the counting device electrically produces unlocking of the locking device based on data stored in the counter device.

16. Nebulizer according to claim 15, wherein said conductors and associated wipers are arranged on a lower end face of the container or a holding element thereon.

* * * * *